United States Patent [19]

Hatch et al.

[11] 4,337,048
[45] Jun. 29, 1982

[54] CAREER OCCUPATION BASIC SKILLS TRAINING SYSTEM

[75] Inventors: James E. Hatch; Thomas W. Gannaway, both of Rochester, N.Y.

[73] Assignee: The Singer Company, Stamford, Conn.

[21] Appl. No.: 196,996

[22] Filed: Oct. 14, 1980

Related U.S. Application Data

[63] Continuation of Ser. No. 27,116, Apr. 4, 1979, abandoned.

[51] Int. Cl.³ .............................................. G09B 19/00
[52] U.S. Cl. .................................... 434/219; 434/224; 434/75
[58] Field of Search .................... 434/219, 224, 72, 73, 434/74, 75, 365, 366, 382, 383, 385, 432, 314, 426, 308

[56] References Cited

U.S. PATENT DOCUMENTS

| | | | |
|---|---|---|---|
| 1,271,641 | 7/1918 | Werwath | 434/224 |
| 1,833,726 | 11/1931 | Stoddard et al. | 434/382 |
| 1,845,240 | 2/1932 | Cook | 434/80 |
| 2,165,003 | 7/1939 | Peters | 434/382 |
| 2,178,255 | 10/1939 | Gibbons | 434/385 X |
| 2,890,531 | 6/1959 | Gracier | 434/75 |
| 3,364,604 | 1/1968 | Donaldson et al. | 434/426 X |
| 3,562,929 | 2/1971 | Emore, Jr. | 434/432 |
| 3,609,740 | 9/1971 | Paine | 434/98 X |
| 3,659,358 | 5/1972 | Brown | 434/74 |
| 3,785,064 | 1/1974 | Thomas, Jr. | 434/383 X |
| 3,864,849 | 2/1975 | Valentine | 434/314 |
| 4,006,537 | 2/1977 | Valentine | 434/314 |
| 4,198,768 | 4/1980 | Wahl et al. | 434/224 |

OTHER PUBLICATIONS

Chemical & Engineering News, Apr. 11, 1977, vol. 55, No. 15, pp. 3, 8, 12, 13, 22, 50, 58, 59.
Webster's Seventh New Collegiate Dictionary, 1965, G&C Merriam Company, Springfield, Mass., p. 981.

Primary Examiner—William H. Grieb
Attorney, Agent, or Firm—David L. Davis; Robert E. Smith; Edward L. Bell

[57] ABSTRACT

The Career Occupation Basic Skills Training System is comprised of a number of open-entry-exit programs designed to meet the pre-vocational and pre-employment needs of the participant. All of the programs are aimed at helping the participant to develop an accurate image of his/her own goals, needs, and skills relative to the world of work. Each of the training programs provides job exploration, occupational awareness, and entry-level preparation through competency building tasks. This is accomplished in a brief amount of time, in a nonthreatening, simulated work environment. At the conclusion of any of the programs, the unskilled participant will have gained much needed information as well as job-getting skills for entry-level positions.

10 Claims, 21 Drawing Figures

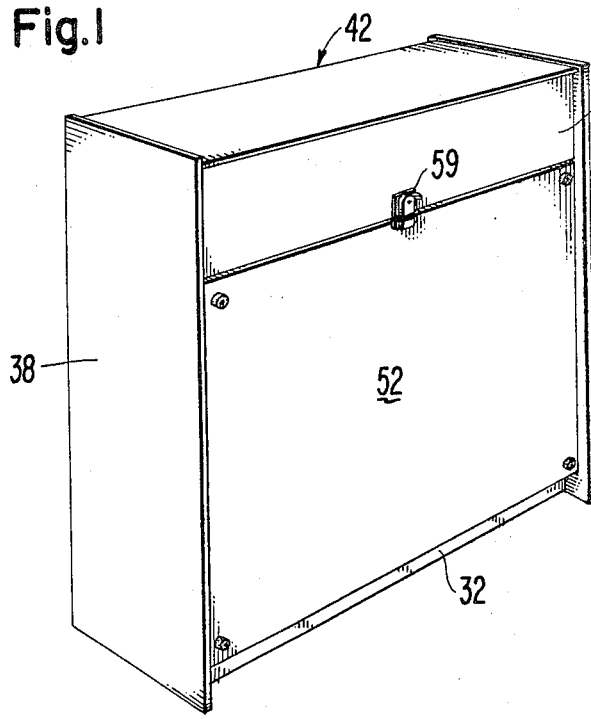
Fig.1
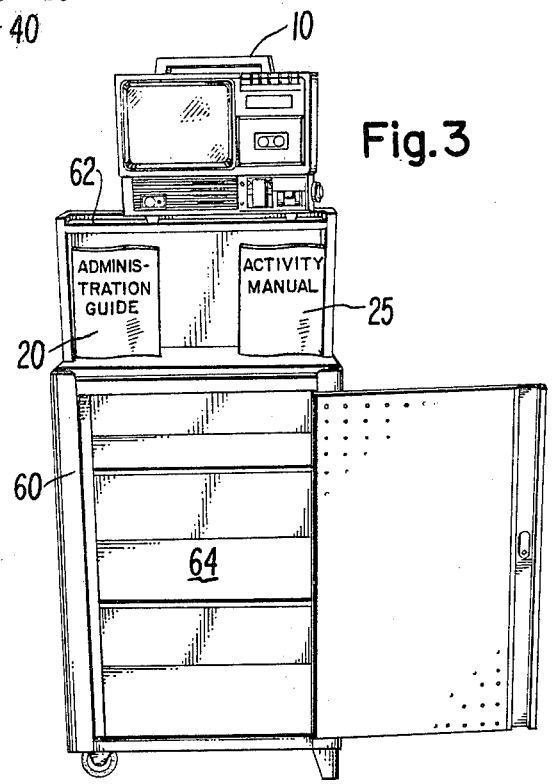
Fig.3
Fig.2

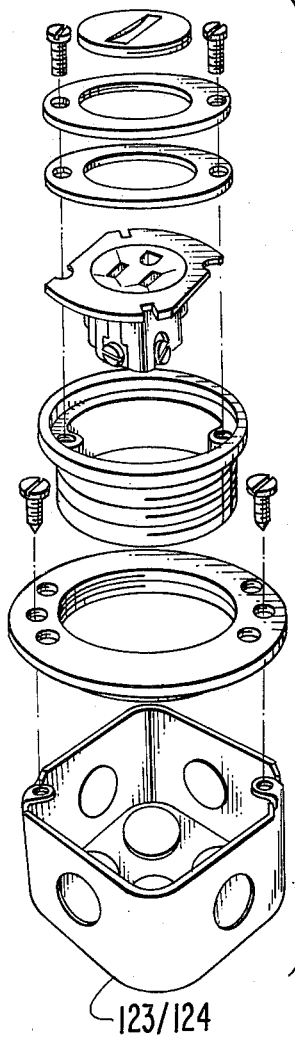
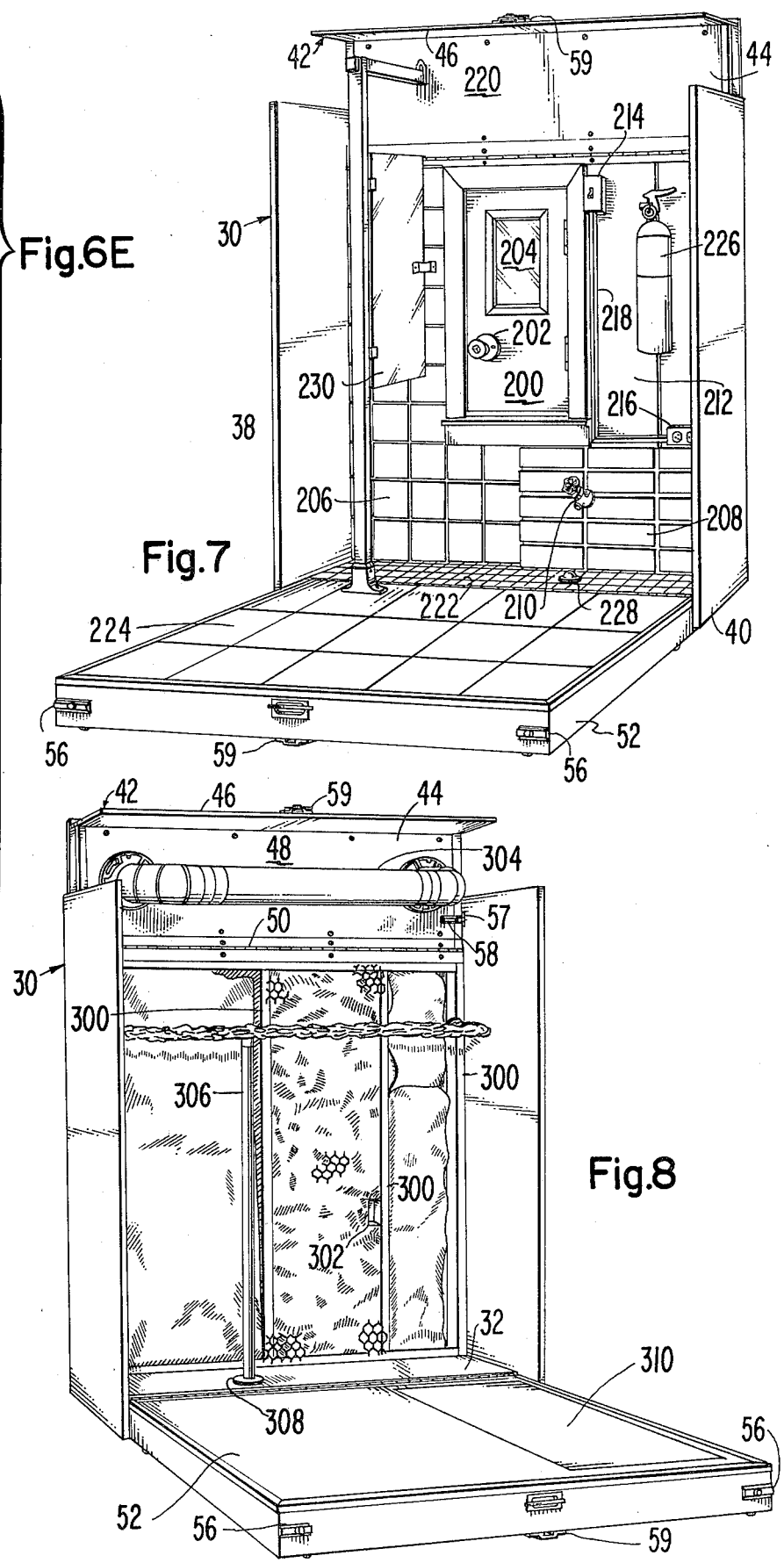

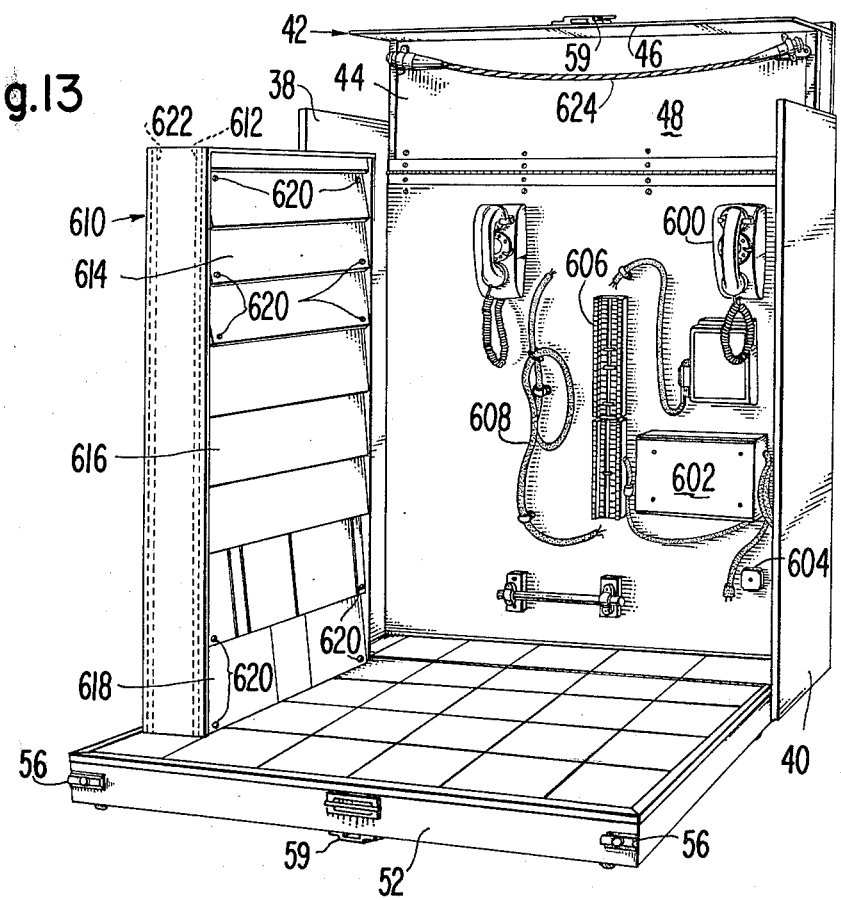

Fig. 14a
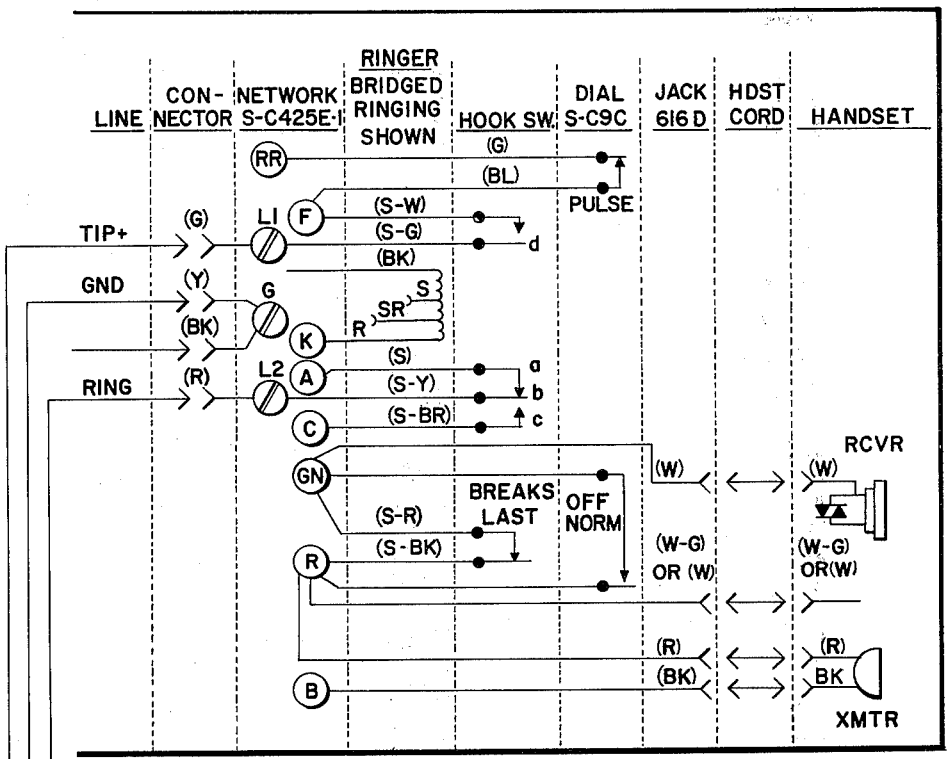
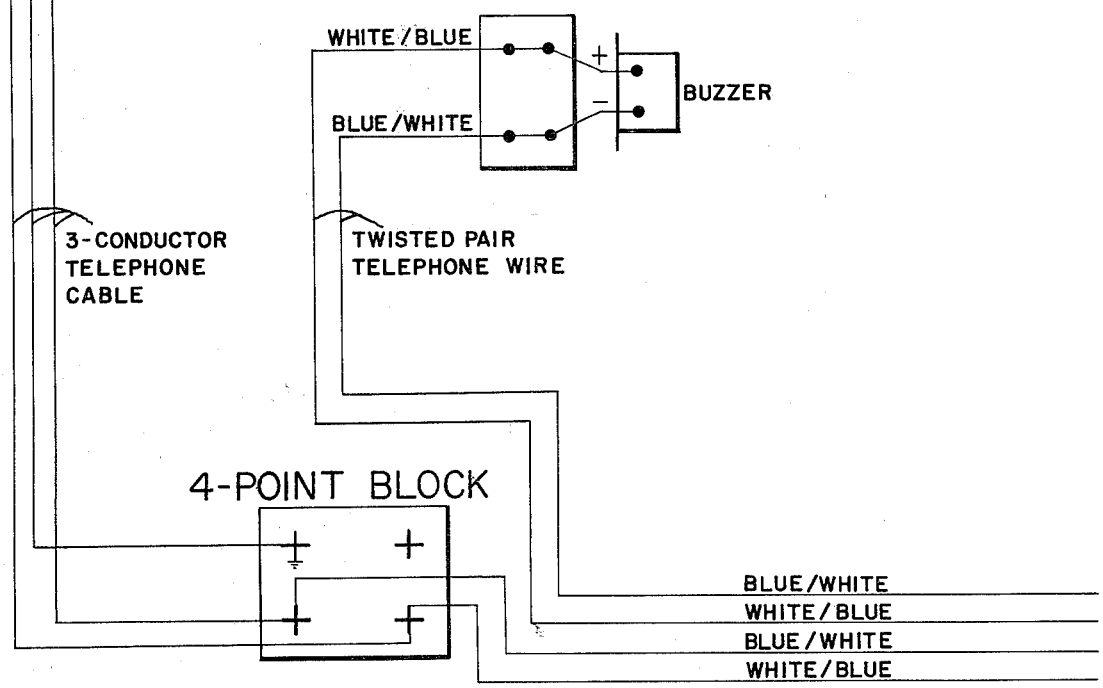

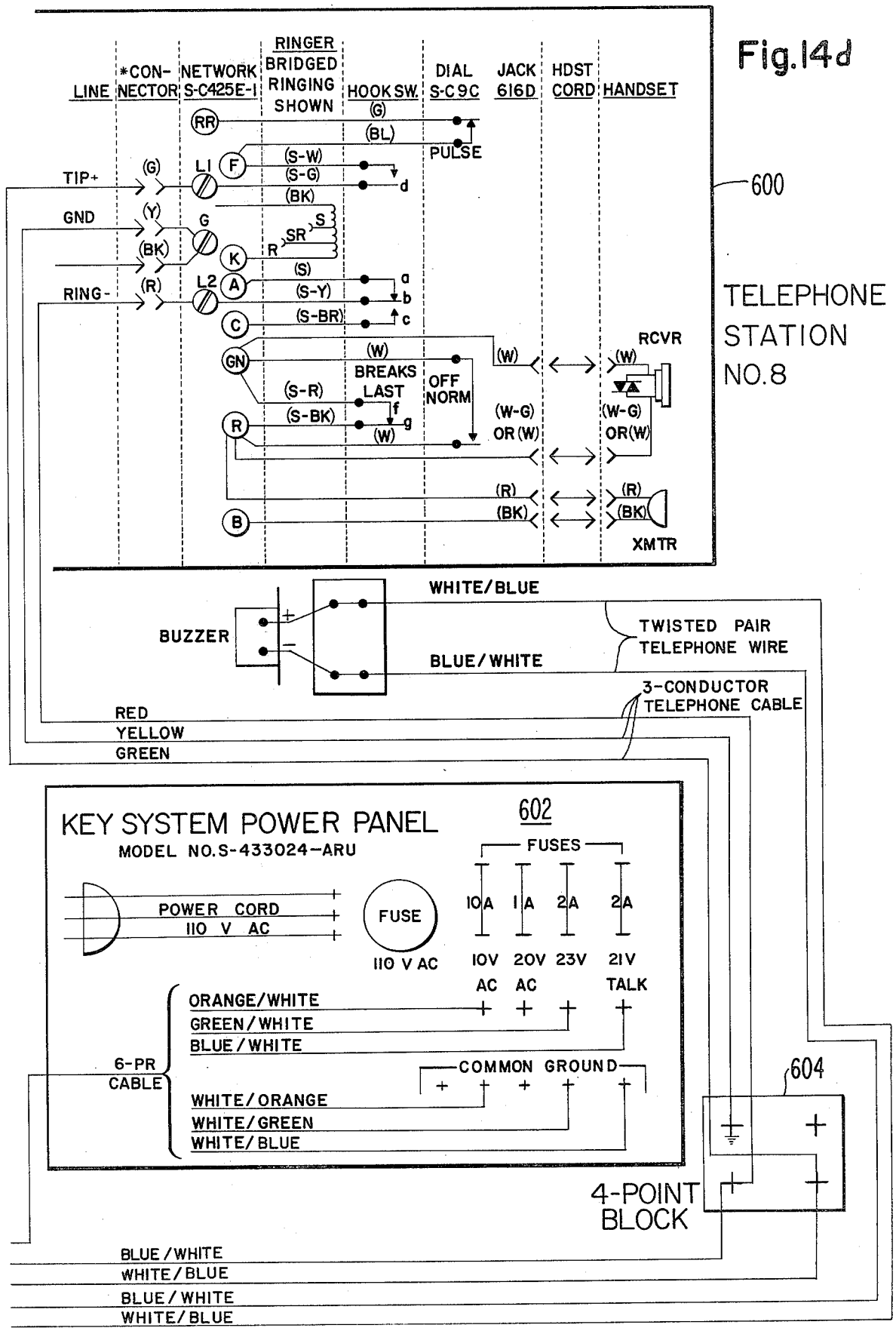

CAREER OCCUPATION BASIC SKILLS TRAINING SYSTEM

This application is a continuation, of application Ser. No. 027,116, filed Apr. 4, 1979 now abandoned.

BACKGROUND OF THE INVENTION

The importance of experience and education in the career decision-making process has been greatly underestimated in our schools and society. Skills needed for this process of obtaining and identifying useful information for judging suitability and selection from two or more possible career choices have not been acquired by the majority of school leavers. The elements of career awareness and career explorations have received attention in many education settings, but the elements of decision-making skills and the relationship of these skills to self-awareness have not been pursued. Little opportunity exists for coordination of these elements or for follow-up activities that include "hands-on" self-exploration and competency building experiences.

Most job seekers, including the school leavers, are expected to make career choices in a very complex technological environment with a diversity of occupations. Frequently, occupational choice is made passively, without the assistance of quality input which includes futuristic occupational information, opportunity to rank alternatives, and having an understanding of the self in a functioning role related to the world of work. Without assistance in this process, options are closed out without adequate consideration of all the occupational choice determinants, particularly opportunities to explore job competencies through skill-building activities. Evidence shows that dispersal of vocational information alone is not adequate to aid career decision-making. Job seekers have the need to learn how to make tentative and flexible career choices within a systematic framework. They need to identify and experience what is important to them in order to make satisfying life and career choices. Making a career choice is one of the most significant acts in a person's life and requires much more than a theoretical base from which to initiate an action plan toward a self-fulfilling and productive life.

SUMMARY OF THE INVENTION

One objective of this invention is to provide specific occupational information and job criteria which depict the changing nature of the occupational society, especially relating to life styles associated with occupations and job classifications.

Another objective of this invention is to provide a systematic means with which to self-test knowledge, abilities, attitudes, and to acquire a more realistic basis for occupational choice.

Another objective of this invention is to provide opportunities to perform various kinds of occupational tasks to develop specific job competencies and to learn specific job-related skills.

Another objective of this invention is to provide learning experiences which can be used to compare a variety of job tasks and performances to specific occupational classifications, toward the gaining of knowledge, appreciation of work standards, and an experience-related base.

These objectives are achieved in a basic skills training system which provides a systematic means for assisting the participant to understand the career decision-making process, a means to learn job information, a means for providing instruction and practice using tools and materials of the trade, a means of tryout and performance of job tasks, a means which provides a matching of interest and ability to specific jobs, and a means for providing job-getting skill information.

DESCRIPTION OF THE DRAWINGS

With the above and additional objects and advantages in mind as will hereinafter appear, the invention will be described with reference to the drawings in which:

FIG. 1 is a front perspective view of the simulator in the closed position;

FIG. 2 is a front perspective view of the simulator in the open position prior to the adaption thereof for each of the programs;

FIG. 3 is a front perspective view of the standard tool cart showing the AV device in place;

FIG. 6E is an exploded perspective view of the floor receptacle to be assembled and installed by the participant;

FIG. 7 is a front perspective view of the opened simulator as adapted for the Building Maintenance program;

FIG. 8 is a front perspective view of the opened simulator as adapted for the Insulation Installation program;

FIG. 13 is a front perspective view of the opened simulator as adapted for the Telephone and Cable TV Services program; and FIG. 14a–14d is a schematic diagram of the wiring of the simulator for the Telephone and Cable TV Services program.

DESCRIPTION OF THE PREFERRED EMBODIMENT

Figure 4:
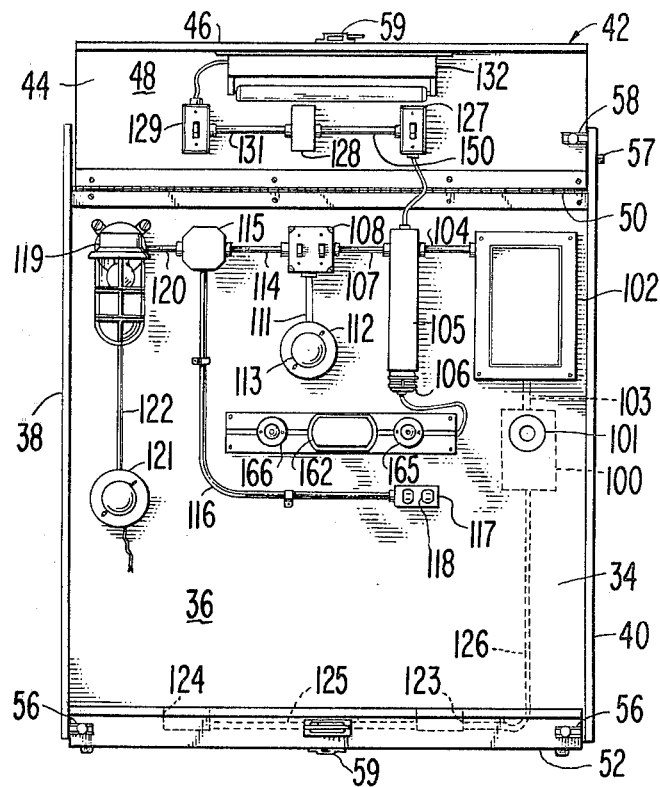
FIG. 4 is a front elevational view of the opened simulator adapted for the Electrical Maintenance program.

The training system of this invention encompasses six career occupation programs including (1) Electrical Maintenance, (2) Building Maintenance, (3) Insulation Installation, (4) Housekeeping Services, (5) Alarm and Signal Systems, and (6) Telephone and Cable TV Service. These occupations are representative of occupational areas that, according to Department of Labor projections for the 1977–1982 time period, have and will continue to have some of the largest numbers of entry-level job openings in the United States.

Each program in the Career Occupation Basic Skills Training System includes the following materials and equipment: an audio-visual (AV) device 10 along with filmsrips and cassette tapes therefor, a remote control foot pedal (not shown) for operating the AV device 10, printed material including an Administration Guide 20 containing a detailed program description for use by an instructor, and an Activity Manual 25 for use by the participant, a work-task simulator 30, and a tool storage cabinet 60 (see FIGS. 1, 2 and 3). Each of the programs also include consumable material (not shown) in amounts sufficient for 30 participants.

Each occupation training program of the disclosed training system is divided into seven separate yet interrelated Units, as outlined in Table 1. A participant may complete any or all of the Units, individually or as part of a group. Each Unit features filmstrips and sound-synched cassette tapes. The printed material found in the Activity Manual 25 is included to reinforce and accentuate the main points of each Unit and to give the participant a basis for self-assessment.

TABLE I

Unit I Introduction: Career Occupation Basic Skills Training System

This unit provides the participant with a brief overview of the Career Occupation Basic Skills Training System. The purpose is to acquaint the participant with the units available in each program and to make him/her aware that there are various activities and tasks to be performed in these units. The filmstrip/cassette tape presentation on the AV device 10 also explains how the participant will benefit from participation in a Career Occupation Basic Skills Training program. Provided with an overview such as this, the participant will better be able to begin a program with a sense of direction and purpose.

Unit II Career Decision-Making Plan

The "Career Decision-Making Plan" is a unit designed primarily to help the participant understand the career decision-making process. The AV device 10 presentation explains to the participant how this program can help him/her in making career decisions, and the presentation also clarifies the following terms and concepts that will be used in the program: "career," "entry level," "decision-making," and "goals."

Unit III Occupational Information

This unit provides in-depth occupational information relating to the specific occupational area of the program. Included is information on entry-level job opportunities, job performance, educational requirements, working conditions, advancement opportunities, and job potential.

Unit IV Tools and Materials

This unit provides instruction and practice in the identification and use of specific occupationally-related tools and materials designated to develop pre-employment competencies.

Unit V Simulated Job Tasks

This unit develops entry-level skills through actual participant "hands-on" application of tools and materials to tasks. The tools, materials, and tasks are designed to replicate those encountered by entry-level workers in that particular occupational area.

Unit VI Matching Occupations to Qualifications

This unit reviews the decision-making model in relationship to the participant's self-awareness obtained in the specific Career Occupation Basic Skills Training program. The participant assesses his/her interests, attitudes, and aptitudes, and this self-assessment is compared with the demands of the occupational area under consideration.

Unit VII Job-Getting Skills

This unit is an overview of the skills and techniques needed to get a job. It helps participants develop their own plans for getting jobs and helps them learn the skills they need to execute that plan.

The AV device 10 presentation covers four major areas: Looking for a job; Preparing for an interview; Having an interview; Following up.

The printed materials in the participant's Activity Manual 25 include a "Guide for Job Hunters," a "Job Fact Card," a vocabulary list of words commonly used on application forms, a list of word definitions, a typical application form, a list of questions often asked by interviewers, and a follow-up letter.

The Units I, II and VII of each program, as outlined in Table I, are standard presentations for all of the programs. The Unit V, "Simulated Job Tasks," will vary from program to program in the number of filmstrips and cassette tapes featured. Because of individual participant abilities and other variants, the length of time that it will take a participant to complete any program will always vary.

The work-task simulator 30, shown in FIGS. 1 and 2, is adapted for use in each of the occupational programs and is a self-contained work station which may be closed during periods of nonuse. The simulator 30 includes a base 32, a rear wall 34 having a removable panel 36 mounted therein, and two sidewalls 38 and 40 rigidly mounted to the base 32 and the rear wall 34. The simulator 30 further includes a top closure 42 having a first section 44 joined perpendicularly along one edge thereof to a second section 46. The first section 44 of the top closure 42, which is formed with a removable panel 48 therein, is pivotally mounted to the top of the rear wall 34 by means of a hinge 50. The hinge 50 allows the top closure 42 to assume a first position in which the first section 44 thereof is coplanar with the rear wall 34 and a second position in which the first section 44 is parallel to and overlies the base 32. The simulator 30 also includes a base apron 52 which provides a work surface for the participant and is positionable in a first position wherein the base apron 52 is coplanar with the base 32 and a second position wherein the base apron 52 is perpendicular to the base 32, extending upwardly therefrom. The base apron 52 and the second section 46 of the top closure 42 are sized such that when each are in the second respective positions thereof, the base apron 52 and the top closure 42 second section 46 abut one to the other (see FIG. 1). Slide bolts 56 are mounted to the base apron 52 for retaining the base apron 52 in the second position thereof. A first keyed pin-lock 55 is also provided for locking the base apron 52 in the second position thereof. An additional slide bolt 58 is mounted to the top closure 42 first section 44 for retaining the top closure 42 in the first position thereof. A second keyed pinlock 57 serves the dual purpose of locking the top closure 42 in both the first position as well as the second position thereof. A sash bolt 59 is mounted to the top closure 42 second section 46 for selectively engaging the base apron 52 when the top closure 42 and the base apron 52 are in the second respective positions thereof.

The tool storage cabinet 60, shown in FIG. 3, for each of the occupational programs except Housekeeping Services, contains a complete set of tools and materials therefor. The tool storage cabinet 60 includes a top shelf 62 upon which the AV device 10 may be placed when using any of the programs. A lockable compartment 64 is provided in the tool storage cabinet 60 within which the tools and materials along with the AV device 10 may be locked during periods of nonuse.

To better understand the invention as disclosed herein, the Electrical Maintenance program will be described in detail in its entirety. Since each of the programs in the Career Occupation Basic Skills Training System is of the same format as the Electrical Maintenance program, the remaining programs will only be generally described with emphasis given to those areas unique to each specific program.

In FIG. 4 the simulator 30 is shown equipped for use in the Electrical Maintenance program. The panel 36 in the rear wall 34 of the simulator 30 has a first circuit breaker box 100 mounted on the reverse side thereof. A power inlet plug 101 is mounted on the front side of the panel 36 directly opposite the circuit breaker box 100 and connects therewith through a hole (not shown) formed in the panel 36. A second circuit breaker box 102 is mounted on the panel 36 above the power inlet plug 101 and is connected to the first circuit breaker box 100 via a conduit 103 passing through a hole (not shown) formed through the panel 36. A conduit 104 connects the second circuit breaker box 102 with a rectangular wireway 105, also mounted to the panel 36. The wireway 105, which includes a doorbell transformer 106 mounted to one end thereof, is connected by a conduit 107 to a switch box 108 mounted to the panel 36. The switch box 108 has two electrical switches 109 and 110 mounted therein and is connected by a first conduit 111 to a junction box 112, having a porcelain light fixture 113 mounted thereon. A second conduit 114 connects the switch box 108 to a junction box 115, which is, in turn, connected by a conduit 116 to an outlet box 117 having a duplex electrical 118 mounted therein. The junction box 115 is further connected to a waterproof light fixture 119 by a conduit 120. A switched light fixture 121 is connected to the waterproof light fixture 119 by a conduit 122.

Two junction boxes 123 and 124, interconnected by a conduit 125, are mounted in the base 32 at the simulator 30 and are connected to the first circuit breaker box 100 by a flexible cable 126.

The removable panel 48 of the top closure 42 first section 44 has tandemly mounted thereon three handy boxes 127, 128 and 129. A conduit 130 interconnects the boxes 127 and 128 and a conduit 131 interconnects the boxes 128 and 129. A flourescent light fixture 132 is mounted to the second section 46 of the top closure 42.

Figure 5:
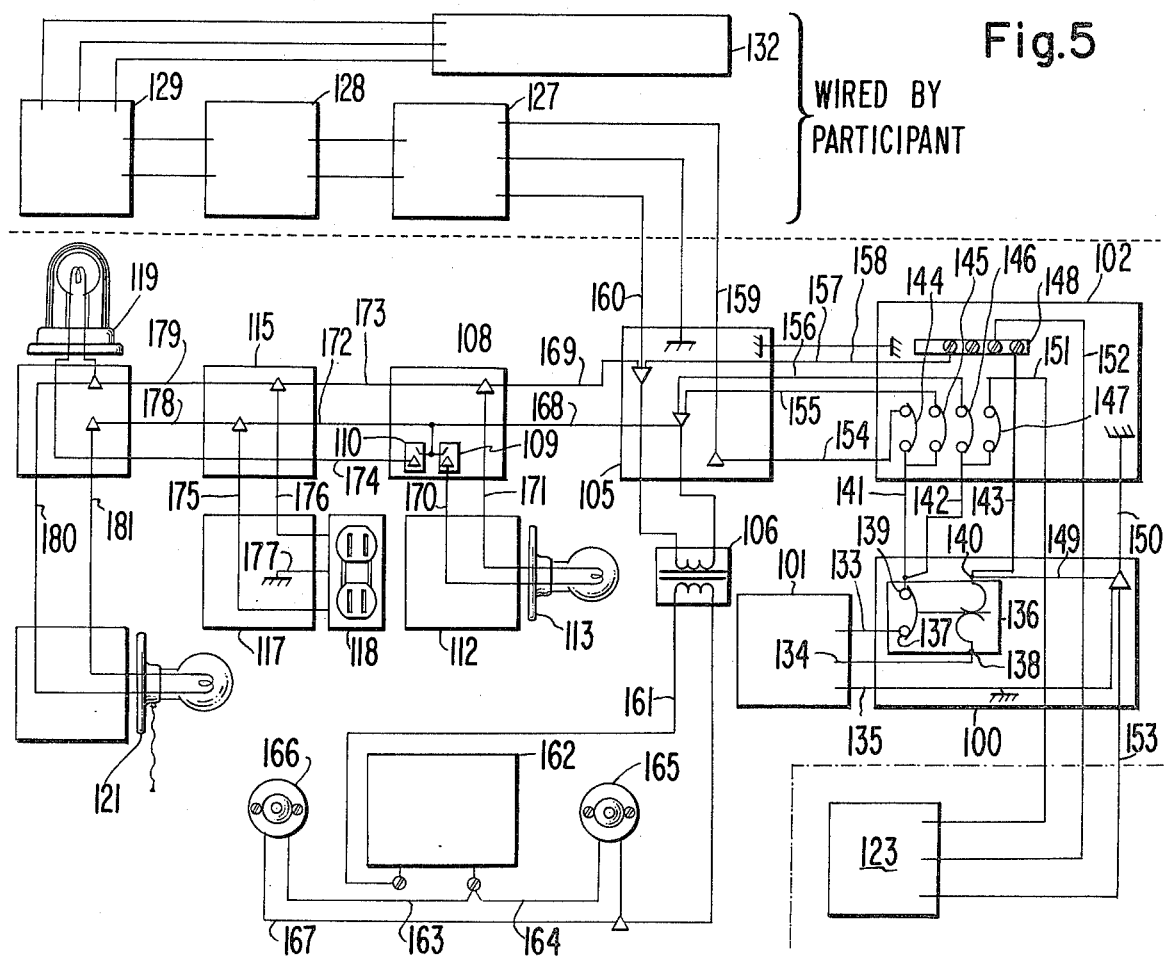
FIG. 5 is a wiring diagram of the modified simulator of FIG. 4.

FIG. 5 is a wiring diagram of the simulator 30 as initially wired by the manufacturers. The power inlet plug 101 is shown as having a black, a white and a green lead, 133, 134 and 135, respectively. The black lead 133 and the white lead 134 are connected to input terminals 137 and 138 respectively, of a ground fault detecting circuit breaker 136 located within the first circuit breaker box 100. The circuit breaker 136, which may be a commercially available item such as, for example, model number Q02-4AS made by the Square-D Company, is capable of detecting both a differential current flow between the high and common side of the electrical power and a leakage current in the ground circuit and thereupon disconnecting the main power. The output terminals 139 and 140 of the circuit breaker 136 have wires 141, 142 and 143 connected thereto which pass through the conduit 103. The wire 141 interconnects the circuit breaker 136 terminal 139 with a first pair of circuit breakers 144 and 145 located within the second circuit breaker box 102. The wire 142 interconnects the circuit breaker 136 terminal 139 with a second pair of circuit breakers 146 and 147 also located within the second circuit breaker box 102. The wire 143 interconnects the circuit breaker 136 terminal 140 with a common bar 148 mounted within the second circuit breaker box 102. The wire 135 is physically grounded to the first circuit breaker box 100. A wire 149 is also connected to the circuit breaker 136 terminal 140 and is spliced to the wire 135 and a wire 150 which passes through the conduit 103 and is physically grounded to the second circuit breaker box 102. A wire 151 is connected to the circuit breaker 147 and passes back through the conduit 103 along with a second wire 152, which is connected to the common bar 148. The wires 151 and 152 are joined by a third wire 153 originating at the junction of the wires 135, 149 and 150, and the three wires 151, 152 and 153 pass through the flexible cable 126 and terminate at the floor junction box 123.

Three wires 154, 155 and 156 are connected one to each of the circuit breakers 144, 145 and 146 and pass through the conduit 104 to the wireway 105. A wire 157 connected to the common bar 148 also passes through the conduit 104 to the wireway 105. A ground wire 158 passes through the conduit 104 and is physically grounded to both the second circuit breaker box 102 and the wireway 105. Within the wireway 105 the wires 154 and 157 are spliced to wires 159 and 160, respectively, for later access by the participant. The wires 155 and 156 are spliced together inside the wireway 105 and are connected to one side of the bell transformer 106 primary winding, the other side of which being spliced to the wire 157. A wire 161 connects one side of the secondary winding of the bell transformer 106 to a bell/buzzer combination 162. Wires 163 and 164 interconnect the bell/buzzer 162 to a pair of bell buttons 165 and 166 which are, in turn, interconnected by a wire 167 terminating at the bell transformer 106 secondary winding.

Wires 168 and 169 are also respectively spliced to the wires 155/156 and 157 and pass through the conduit 107 to the switch box 108. The wire 168 is connected to one side of both of the switches 109 and 110. A wire 170 is connected to the other side of the switch 109 and along with a wire 171, which is spliced to the wire 169, pass through the conduit 111, into the junction box 112 and are connected to the light fixture 113. Wires 172 173 and 174, which are respectively connected to wires 168, 169 and the switch 110, pass through the conduit 114 into the junction box 115. The wires 172 and 173 are then spliced respectively to wires 175 and 176 which pass through the conduit 116 into the outlet box 117 and are connected to the duplex outlet 118. The outlet 118 is physically grounded to the outlet box 117 by a wire 177. Wires 178 and 179 are respectively spliced to the wires 172 and 173 and pass along with wire 174 through the conduit 120 to the light fixture 119. The wire 174 is connected directly to the fixture 119. The wire 179 is connected to the fixture 119 and is spliced to a wire 180 which, along with a wire 181 spliced to the wire 178 pass through the conduit 122 and connect to the light fixture 121.

In using the Electrical Maintenance program, the participant proceeds through the standard Units I and II as outlined in Table 1. After the filmstrip and the cassette tape presentation of Unit III on the AV device 10 also as outlined in Table 1, the participant completes a questionnaire in the activity manual 25 relating to the presentation.

In Unit IV the participant is introduced to all of the tools and materials that he/she will use during the rest of the program. Additionally, the unit describes several tools which the participant does not actually use but should know about.

The Unit begins with an audiovisual presentation that shows, names, and explains the use of various tools and materials commonly used in the electrical maintenance field. During the unit, the participant performs four brief tasks: stripping wire, stripping cable, attaching (using connectors) conduit and cable to a box, and wiring a three-prong male cap. These activities duplicate tasks which are very common for electrical workers, and they provide practice for tasks which will be performed in subsequent units. In addition, these tasks should help to generate interest in the program.

At the end of the filmstrip, the participant will complete a matching exercise called the "Self-Assessment Activity" in the Activity Manual 25. In this exercise the participant matches drawings of the tools discussed in the filmstrip to their printed names. The participant keeps the "Self-Assessment Activity" and should correct any wrong answers as he/she goes through subsequent units in the program. A second, identical "Self-Assessment Activity" is administered at the end of the Job Task unit for comparison and assessment of learning.

Figure 6A:
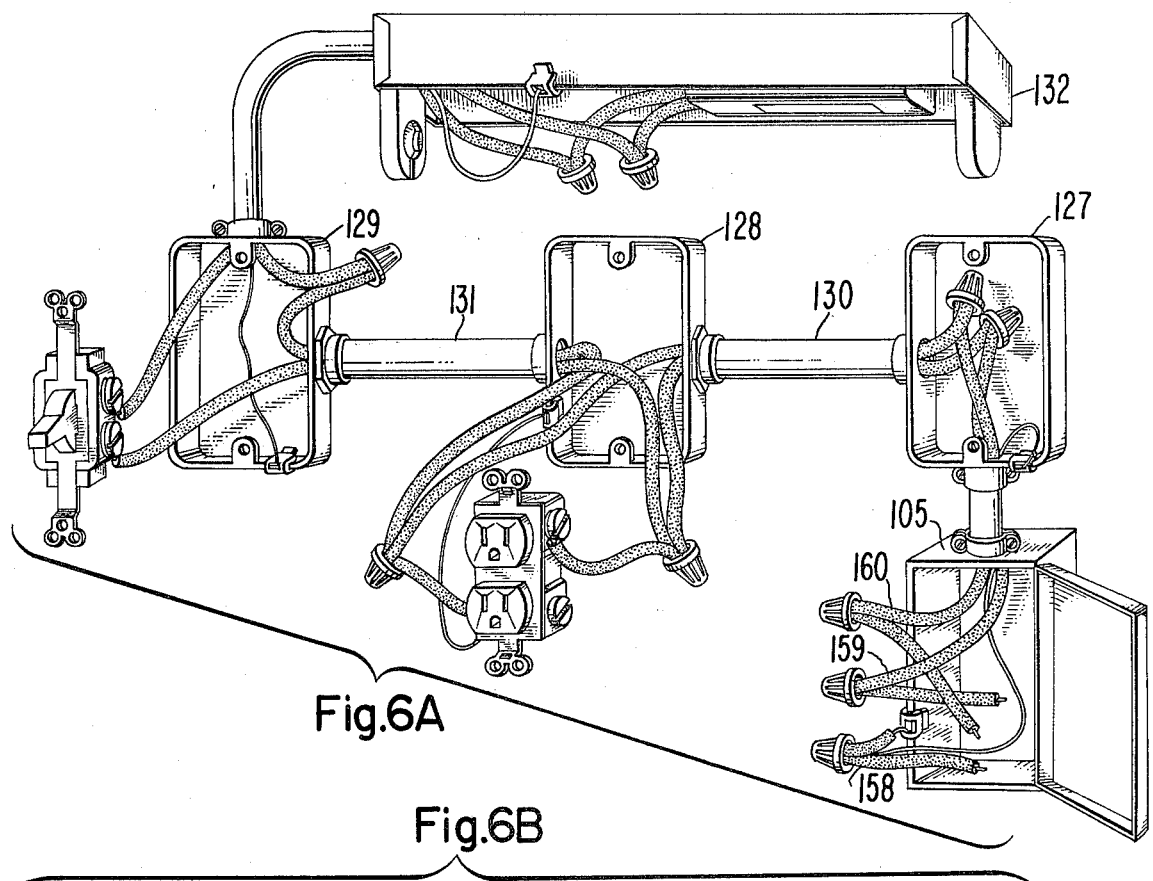
FIG. 6A is a diagramatic view of circuit 1 to be wired by the participant.
Figure 6B:
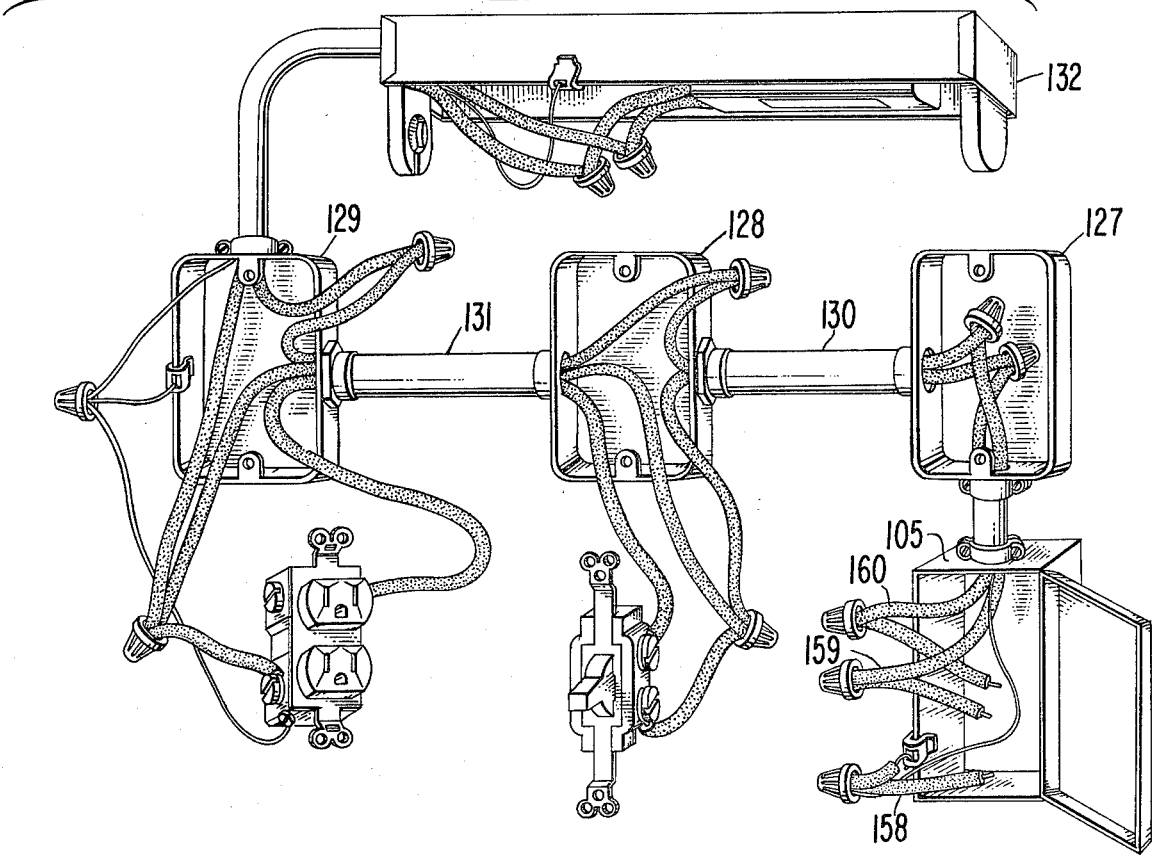
FIG. 6B is a diagramatic view of Circuit 2 to be wired by the participant.

In Unit V the participant wires three different circuits on the work-task simulator (see FIGS. 6A, 6B, and 6E). The first and second circuits both use the three handy boxes 127, 128 and 129 at the top of the simulator 30. For the first circuit, a hot receptacle and a switched fluorescent light 132, the audiovisual presentation gives step-by-step instructions; each step is related to a detailed illustration of the circuit. In the second circuit the position of the switch and receptacle are reversed, requiring the addition of a second hot wire. For this, the participant receives fewer instructions and must rely more heavily on the circuit illustration for directions. The third circuit requires each participant to install and wire receptacles in the two floor boxes 123 and 124. The presentation gives detailed instructions on using a fish tape to pull wires through the concealed, sub-floor conduit. For assembling and wiring the receptacles, however, the participant must follow a sheet of simulated manufacturer's instructions as shown in FIG. 6E.

At the end of this portion of the Unit, each participant completes the "Basic Wiring Self-Assessment" activity in the "Job-Tasks" Unit in the Activity Manual 25, in this activity the participant evaluates how well he/she performed the tasks and how well he/she liked the tasks.

The audiovisual presentation in this Unit now describes, as simply as possible, the function of the components in a basic residential or commercial electrical system. Basic terms related to electrical theory and practice are introduced and explained. All of these terms and concepts are likely to be encountered in the first six months of work in the electrical field. A water-system analogy, used throughout the unit, simplifies and clarifies the behavior of electricity.

A series of written activities, which are interactive with the filmstrip, is included in the participant's Activity Manual 25. For each activity, there is a brief written summary of the information which was presented audiovisually.

Figure 6C:
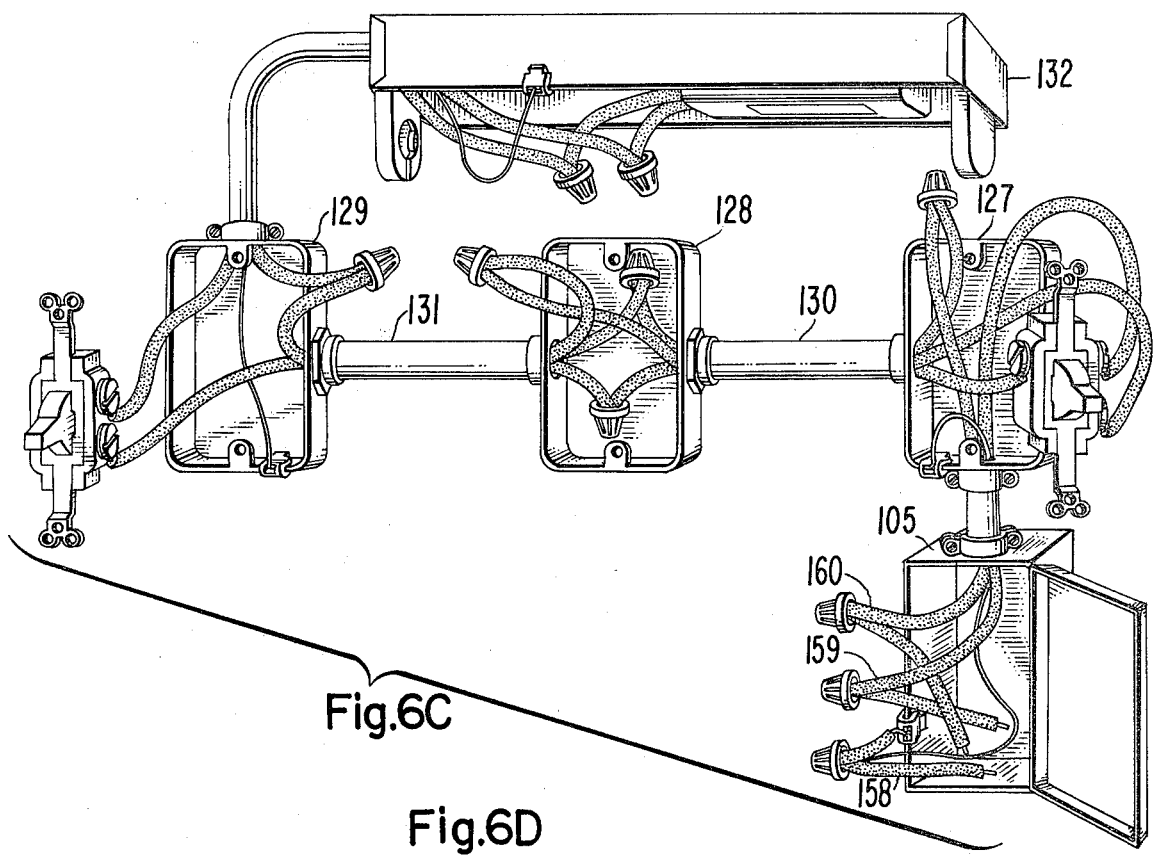
FIG. 6C is a diagramatic view of Circuit 3 to be wired by the participant.
Figure 6D:
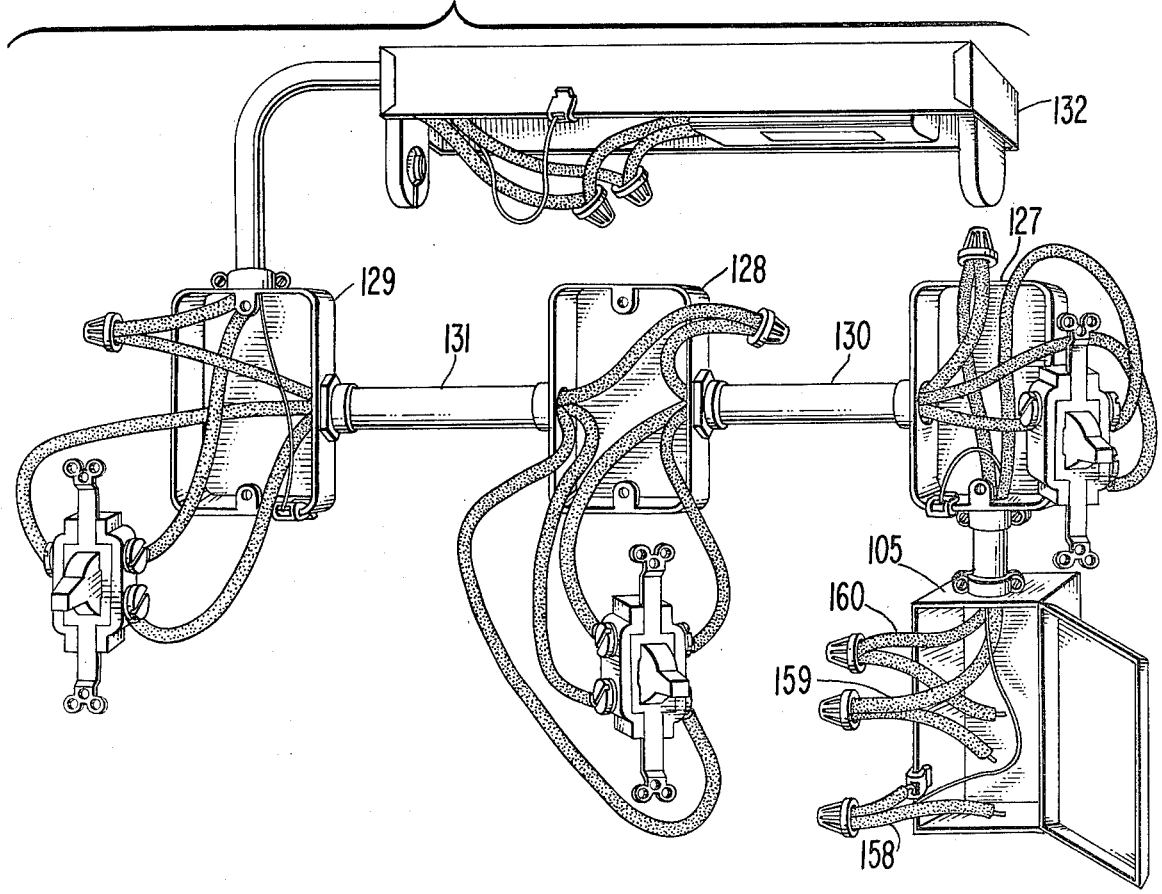
FIG. 6D is a diagramatic view of Circuit 4 to be wired by the participant.

The Unit now introduces three-way and four-way switching. The participant begins by using a continuity tester to discover the action of a three-way switch. Next, he/she wires two three-way switches together and checks them with the continuity tester. Then, he/she wires a three-way switching circuit on the work-task simulator 30 as shown in the drawing in the Activity Manual 25 (see FIG. 6C). A short cartoon sequence introduces a four-way switching circuit on the work-task simulator 30 (see FIG. 6D). This simply requires connecting a four-way switch to wires already in place in the three-way circuit. For each circuit, the participant must use an illustration for direction; only minimal wiring instructions are given audiovisually.

The final portion of the Unit of the program has no filmstrip or tape. Its content and administration are left to the instructor's own initiative and imagination. The program instructor selects tasks for the participant to perform on the two permanently wired circuits in the center of the work-task simulator. The tasks selected will naturally be based on the instructor's knowledge of electrical work and his/her estimate of the participant's interests and abilities.

The problem setups listed below create electrical maintenance tasks commonly found in entry-level work. The problem setups are listed in order of increasing difficulty for repairs.

Insert a dead lightbulb in one of the sockets.

Trip a circuit breaker. (This can be easily done by removing the cover of the circuit breaker box 102, pulling out one of the circuit breakers, 144, 145, 146, 147 and pushing it back onto its poles; the breaker will trip automatically. Replace the cover. Naturally, the instructor must make sure the power cord is disconnected.)

Disconnect a wire from one of the devices or from several devices.

Reverse the positions of two wires on a device.

Replace one of the switches with a defective switch. (If an already defective switch is unavailable, take a good switch apart: Remove the small machine screws which hold the two halves of the plastic body together, and slowly separate the halves. Inside is a small, springy piece of metal which connects the poles of the switch; this normally pops out when the switch is taken apart. Throw it away and screw the switch back together again. If this is done, the switch should be marked or somehow identified as defective, and kept apart from the other switches.)

In Unit VI, "Matching Occupations to Qualifications", the participant assesses his/her work interests, attitudes, and aptitudes and compares them to the demands of the Electrical Maintenance field. Then, by following the Career Decision-Making Plan introduced in the second Unit, the participant should be able to determine his/her interest in pursuing work in Electrical Maintenance.

Finally, the participant receives training in Unit VII for the skills and techniques needed to get a job, as outlined in Table 1.

The Building Maintenance program is sustantially similar in format to the Electrical Maintenance program, as set forth in detail above. The work-task simulator 30, as equipped for the Building Maintenance program is shown in FIG. 7. The removable panel 36 in the simulator 30 rear wall 34 has a "scaled-down" door 200, complete with a lockset 202 and a glass pane 204, installed therein centered along the top edge thereof. Ceramic wall tiles 206 are mounted to the removable panel 36 to the left of and partly beneath the door 200. The remaining area of the panel 36 beneath the door 200 is covered with hacienda-type bricks 208. A garden faucet 210 is mounted in the brick surface 208 by any suitable means. The area of the removable panel 38 to the right of the door 200 is covered with birch paneling 212. A switch 214 is mounted to the paneling 212 and is connected to a duplex outlet 216 by a wire mold 218. The removable panel 48 in the top closure 42 is replaced by a similarly sized sheet of drywall 220. The base 32 of the simulator 30 is covered with ceramic floor tiles 222, while the base apron 52 is covered with asphalt floor tiles 224.

The work tasks to be performed by the participant are divided into three parts. In part 1, the participant is introduced to a variety of tasks that are common for a building maintenance worker; the participant performs these tasks on the work-task simulator 30. Specifically, the participant performs the following tasks:
repairs a hole in the drywall 220 and spot paints the repaired surface;
replaces a damaged ceramic wall tile 206 and one of the floor tile 222;
removes, fits, and replaces one of the asphalt floor tile 224;
fills holes in the paneling 212;
points up the bricks 208 with mortar;
grouts tile joints;
drives a nail into the paneling 212; and,
caulks between the ceramic wall tiles 206 and the floor tiles 222.

Such "hands-on" experience provides the participant with an opportunity to become familiar with and competent in the use of tools common to building maintenance workers.

In part 2, the participant repairs, inspects, and installs variety of items associated with building maintenance. The audiovisual presentation provides the participant with detailed instructions for performing these tasks on the work-task simulator 30. Specifically, the tasks to be performed in the unit are:
lubricating a squeaky door 200;
lubricating the lockset assembly 202;
replacing the glass 204 in the door 200;
repairing a leaky faucet 210;
checking the switch 214 and replacing it if defective;
mounting a fire extinguisher 226 on the paneled surface 212; and,
mounting a doorstop 228 in the ceramic floor surface 222.

As the participant progresses through the unit, fewer instructions are given on the use of the tools of the trade. The participant is expected to exhibit a high degree of competency using the electric drill, screwdrivers, and hammer.

Part 3 is the most difficult of the "hands-on" tasks. In this unit the participant installs a lavatory partition 230 on the work-task simulator 30. To accomplish this, the participant must perform a series of subtasks which a building maintenance worker would often be expected to perform. These sub-tasks require the use of nearly all the common tools provided with this program. For each sub-task the participant receives minimal audiovisual instruction and must rely on previous experiences within the program. Specifically the participant does the following:
assembles a typical lavatory partition 230, using an assembly drawing as a reference;
performs a series of measuring sub-tasks to position the lavatory partition 230;
uses a variety of appropriate fasteners to mount brackets in drywall 222, ceramic tile 206, and asphalt tile 224 surfaces; and,
uses a level and combination square to determine accurate locations for installing the partition 230. (The participant performs compound sub-tasks such as squaring and fastening, plumbing a post and marking its location, and leveling and anchoring the partition 230.)

At the completion of this Unit, the participant fills in a self-assessment sheet which lists the tasks performed in this program. The participant assesses how well he/she did in performing the tasks and how well he/she liked performing the tasks. Additionally, the participant should complete the second tools and materials "Self-Assessment Activity." Both activities are in the "Job Tasks" Unit of the Activity Manual 25.

The work-task simulator 30 for the Insulation Installation program is shown in FIG. 8. For this program, the panel 36 is removed from the simulator 30. In the opening left by the panel 36, 2×4 studs 300 are vertically mounted on 16 inch centers. An electrical box 302 is mounted to the side of one of the studs 300 approximately 12 inches above the simulator 30 base 32. Galvanized pipe 304 is installed in the top closure 42 removable panel 48. Copper pipe 306 in the shape of a "T" is installed in the simulator 30 using pipe flanges 308 wherein the bottom of the pipe assembly 306 is fastened to the simulator 30 base 32 and the two ends of the "T" portion of the pipe assembly 306 are fastened to two of the studs 300. The base apron 52 is also modified such that there is a removable panel 310 set therein.

In this program the participant performs a number of tasks that closely simulate work done by professionals in the insulation field. The panel 310 in the base apron 52 is pried up, and the space below is filled with cellulose insulation. The panel 310 is then replaced and nailed down. Roll insulation is measured, cut, and stapled between the studs 300. A second piece of insulation is installed with the vapor barrier reversed, and is held in place with chicken wire. A section of this piece must be cut to fit around the electrical box 302. Scrap pieces of insulation are used to fill an odd-sized space, with duct tape applied to keep the vapor barrier intact. Different fastening methods are employed to apply two different types of pipe insulation to the copper pipes 306 in the work-task simulator 30. Finally, foil-faced insulation is measured and cut to fit around the duct work (galvanized pipe 304) at the top of the simulator 30.

At the end of the Unit, the participant completes an activity called "Insulation Skills Self-Assessment." The participant rates him/herself on how well he/she performed each task and how well he/she liked each task. Additionally, the participant should complete the second tools and materials "Self-Assessment Activity." Both activities are in the "Job Tasks" Unit of the Activity Manual 25.

Figure 9:
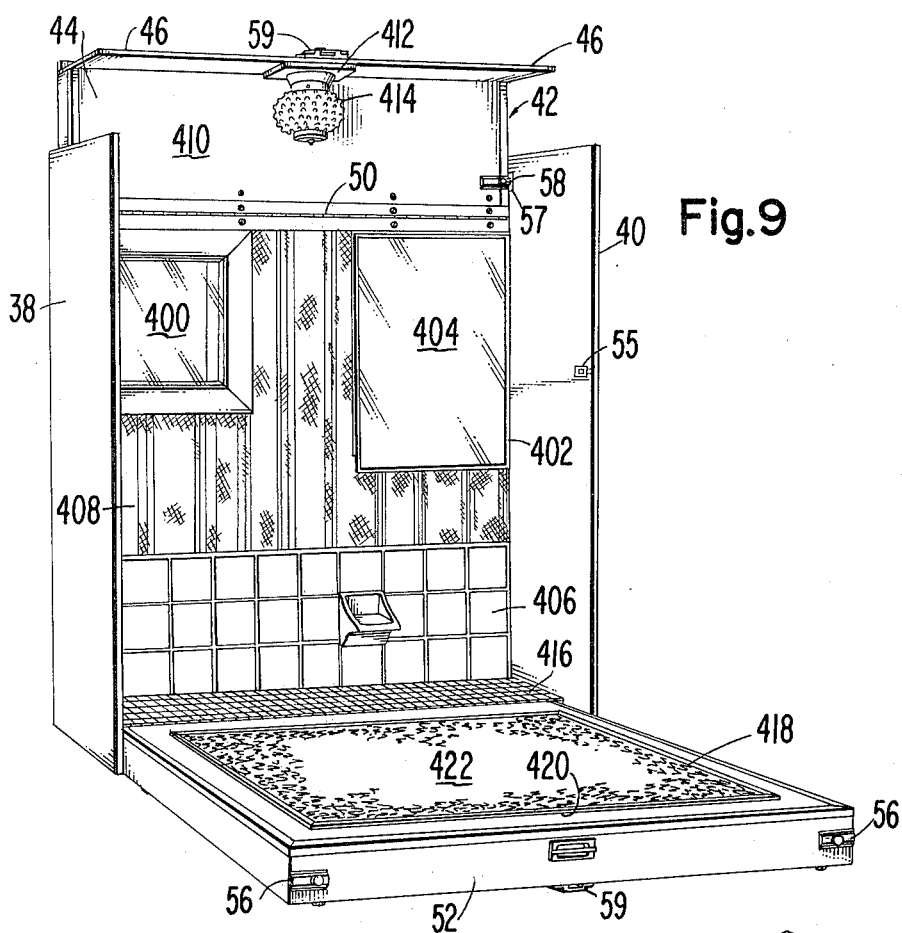
FIG. 9 is a front perspective view of the opened simulator as adapted for the Housekeeping Services program.

The work-task simulator 30 for the Housekeeping Services program is shown in FIG. 9. The removable panel 36 in the simulator 30 has a fixed window 400 set in the upper left corner thereof. A medicine cabinet 402, faced with a mirror 404, is set in the upper right corner of the panel 36. Ceramic tiles 406 are mounted along the bottom of the panel 36 up to a height of twelve inches. The remaining surface of the panel 36 is covered with vinyl wallpaper 408. The removable panel 48 in the top closure 42 is replaced by a similarly sized sheet of drywall 410. The second section 46 of the top closure 42 has a ceiling fixture 412 with a glass globe 414 center thereon. Ceramic tiles 416 are used to cover the base 32 of the simulator 30. For this program, the base apron 52 is modified to have a reversible panel 418 set therein. Asphalt tiles 420 are mounted to one side of the panel 418 while the opposite side of the panel 418 is covered with rubber-backed carpet 422.

Figure 10:
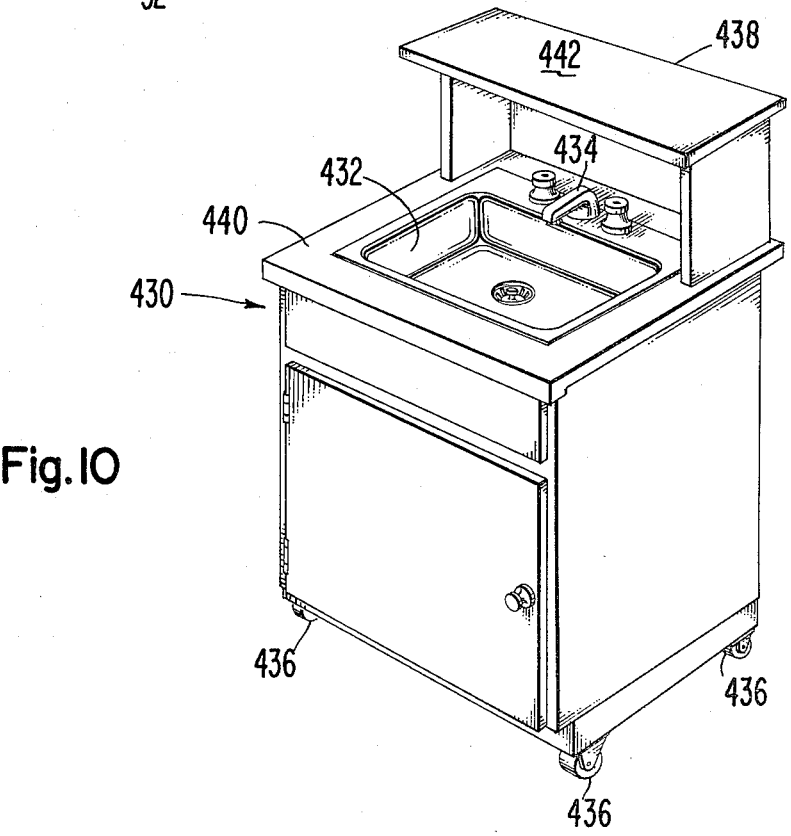
FIG. 10 is a front perspective view of the vanity for use with the Housekeeping Services program.

In substitution for the standard tool storage cabinet 60 as described earlier, a bathroom vanity 430 is provided for this purpose. As shown in FIG. 10 the vanity 430, complete with a sink 432 and a faucet set 434, is modified to include casters 436 on the bottom thereof and a shelf 438 overhanging the rear portion of the top 440 of the vanity 430. Standard grade formica 442 is used to cover both the shelf 438 and the area of the top 440 surrounding the sink 432.

In this part of the program the participant performs the first six tasks listed on the "Work Schedule," which is in the "Job Tasks" unit of the Activity Manual 25. The audiovisual presentation explains the purpose and use of work schedules, provides detailed instructions for performing each task, and also describes other tasks and/or methods that a participant might encounter "on the job." Specifically, the participant performs the following tasks:

sweeps and cleans the carpet 422;
cleans the light fixture 412;
dusts and polishes;
washes walls;
washes the window 400; and,
cleans the mirror 404.

The participant now completes the remaining tasks listed on the "Work Schedule." Again the audiovisual presentation provides instructions for performing each task and describes other tasks and/or methods that a participant might encounter "on the job." Specifically, the participant performs the following tasks:

broom sweeping;
dry mopping;
stripping floor wax;
washing floor tile 420;
waxing asphalt tiles 420; and,
cleaning the sink 432 and vanity cart 430.

When the participant completes the Unit, the instructor will be asked to approve his/her work and sign the "Work Schedule."

At the end of the Unit, the participant completes the "Housekeeping Self-Assessment" activity in which he/she assesses how much he/she liked the various housekeeping tasks and how well he/she performed each of them. The participant also completes the second products and equipment "Self-Assessment Activity," to be used for comparison and assessment of learning. Both activities are in the "Job Tasks" Unit of the participant's Activity Manual 25.

Figure 11:
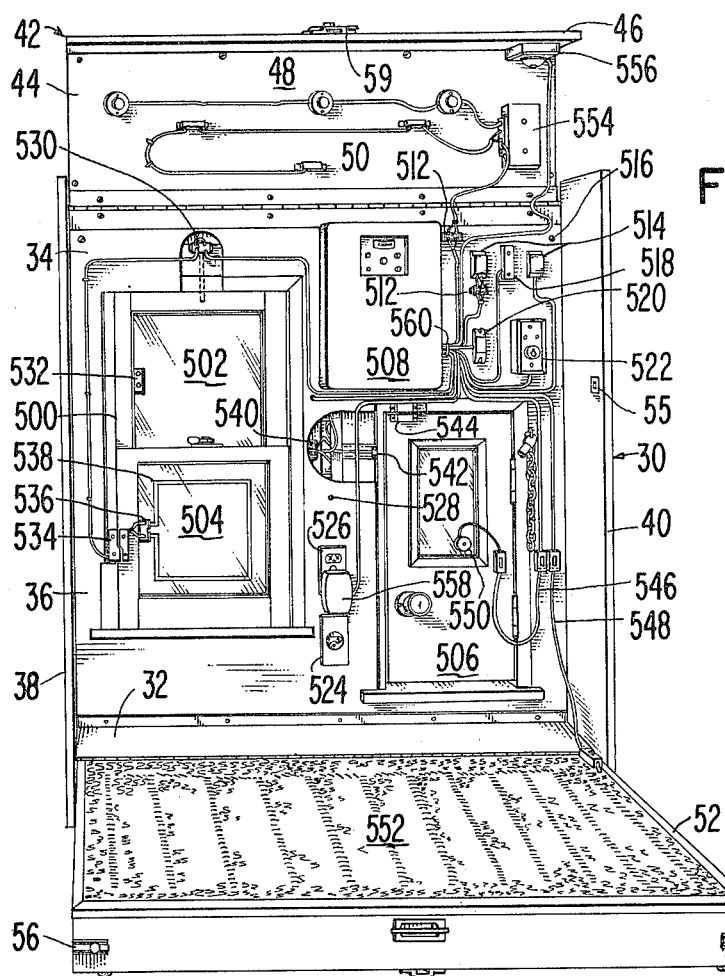
FIG. 11 is a front perspective view of the opened simulator as adapted for the Alarm and Signal Services program.
Figure 12:
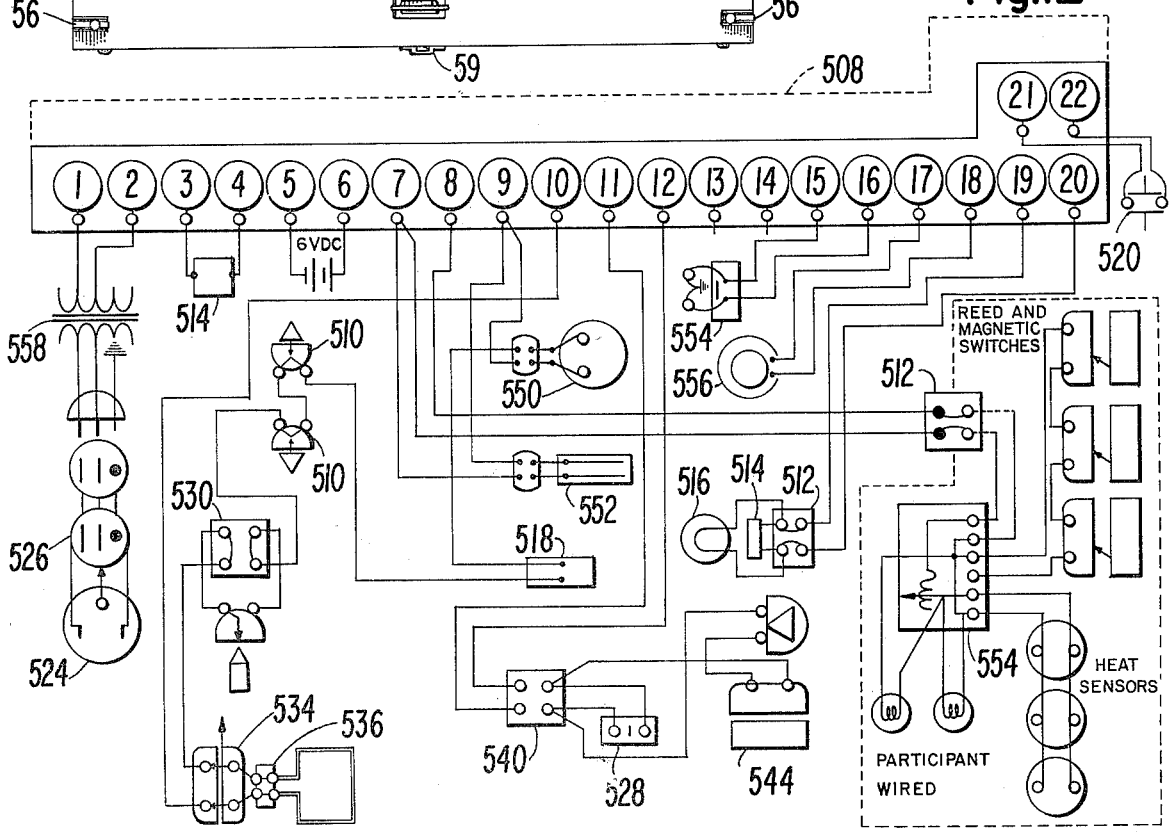
FIG. 12 is a schematic diagram of the wiring of the simulator for the Alarm and Signal Services program.

The work-task simulator 30 for the Alarm and Signal Services program is shown in FIG. 11. The removable panel 30 of the simulator 30 has a window 500, having an upper sash 502 and a lower sash 504, mounted therein. A "scaled down" door 506 is also mounted in the panel 36. Centered along the top edge of the panel 36 is an alarm control panel 508 having two tamper switches 510 positioned behind the cover thereof. Positioned to the right of the control panel 508 are a pair of terminal strips 512, a pair of buzzers 514, a pilot light 516 positioned above one of the buzzers 514, and a vibration sensor 518. Also located to the right of the control panel 508 are an emergency button 520 and a remote control 522. A power inlet 524 is mounted at the bottom of panel 36 between the window 500 and the door 506. A duplex outlet 526 is located above the power inlet 524 and a shunt lock 528 is located above the outlet 526. At the top of the window 500, above the upper sash 502. There is a cutout in the panel 36 exposing a terminal strip 530. A two-terminal foil take-off block 532 is mounted to the window 500 upper sash 502. A set of sliding contact blocks 534 are mounted along the edge of the window 500 lower sash 504 which also has a two terminal foil take-off block 536 along with leaded window foil 538 mounted thereon. The panel 36 has an additional cutout adjacent the upper left corner of the door 506 exposing a terminal strip 540 and a bullet sensor 542 for engaging the door 508. A reed and magnetic contact 544 is mounted along the upper edge of the door 506. A pair of door cords 546 and 548 are mounted to the panel 36 to the right of the door 506. The door cord 546 connects with a window bug 550 mounted to a window in the door 506. The door cord 548 is connected to a pressure sensitive mat 552 which is mounted on the base apron 52. The removable panel 48 in the top closure 42 of the simulator 30 has a relay box 554 mounted thereon while the top closure 42 second section 46 has a heat detector 556 mounted thereon. A transformer 558 is shown plugged into the duplex outlet 526 and supplies power to the control panel 508. Wires from the various sensors and detectors are grouped together into a cable harness 560 which enters the control panel 508. FIG. 12 illustrates the electrical wiring performed by the manufacturer on the simulator 30.

This program introduces the participant to a variety of Alarm and Signal System equipment. The participant is shown how different components on the work-task simulator 30 join together to form the Alarm and Signal System. The participant will install integral system components on the work-task simulator 30 and will test others to develop a basic knowledge of how these different components work in concert.

First, the participant mounts the control panel 508 to the removable panel 36 of the work-task simulator 30. Then, using as a guide the printed form in the Activity Manual 25 called "Control Panel Wiring Chart," he/she connects the wires in the cable harness 560 to the proper terminals on the terminal strip. The participant installs a tamper switch 510 in the control panel 508 and connects the wiring. The participant next installs a transformer 558 and connects it into the system. By plugging one end of an extension cord into the recessed power inlet 524 on the simulator 30 and the other end into a wall receptacle, the participant connects power to the work-task simulator 30. After the participant installs a dry cell battery in the control panel 508, he/she checks the various perimeter intrusion devices to ensure that they are all in the proper position so that the alarm system can be put into the circuit test state. If a particular device is not in the proper position, the participant is given instructions on how to correct the situation.

In this portion of the filmstrip presentation the participant learns in more detail the various parts of residential and industrial alarm and signal systems. Components and their features are discussed in relation to their inclusion in the system. The participant checks the standby power supply, then disconnects it and the pressure sensitive mat 552 from the system. The operation of the perimeter intrusion devices and heat detectors 536 is explained, and the participant tests each device for correct operation.

The participant is now shown how to apply leaded window foil 538 to a glass surface and wire it into the alarm and signal system. The participant draws a chalk outline on the upper sash 502 of the double-hung window 500 and practices foiling the window 502 him/herself. The participant then uses the continuity tester to check for breaks or cracks in the foil 538. If there are breaks in the foil 538, the participant is instructed to fix them.

In the last portion of this program the participant, measures, cuts, and strips cable and wire to construct a series intrusion circuit and a parallel fire alarm circuit on the top closure 42 of the work-task simulator 30. The audiovisual presentation of the unit describes, as simply as accuracy permits, the basic electrical theory of series and parallel circuits. The participant is given an overview of how both kinds of circuits are used in commercial and residential alarm and signal systems, and the participant is introduced to such basic electrical terms as current, conductor, load, circuit, and open and closed circuits.

At the completion of this unit, each participant fills in a self-assessment sheet which lists the tasks performed in this program. The participant assesses how well he/she did in performing the tasks and how well he/she liked performing the tasks. Additionally, the participant should complete the second tools and materials "Self-Assessment Activity."

Figure 14B:
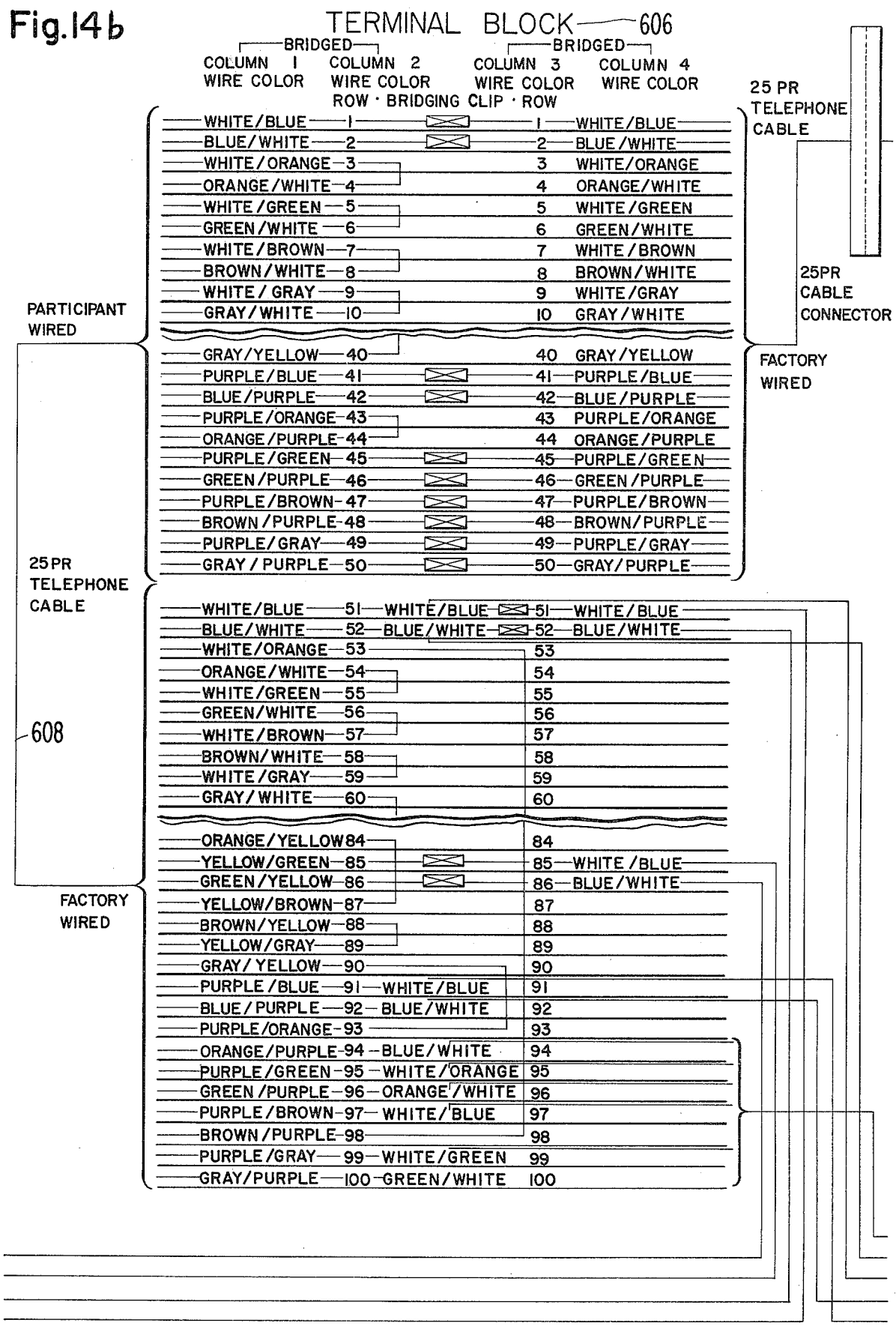
Figure 14C:
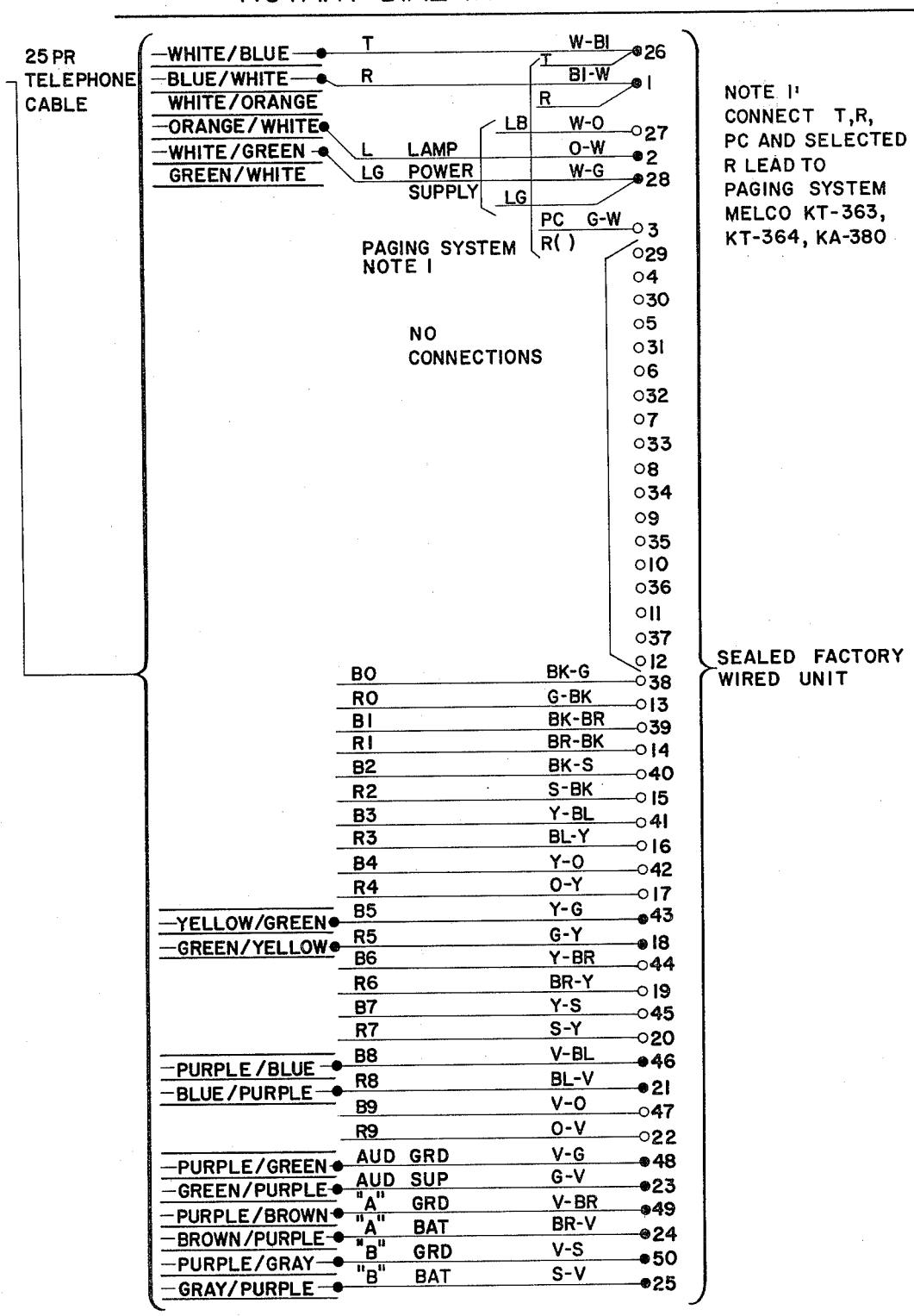

The work-test simulator 30 for the Telephone and Cable TV Services program is shown in FIG. 13. The removable panel 36 has installed thereon a wall phone 600 in the upper right corner thereof, a power supply module 602 spaced below the phone 600, and a 4 point block 604 spaced below the power supply module 602. Two 10 inch terminal blocks 606 are tandemly mounted in a vertical plane adjacent the power supply module 602 to the left thereof. Also attached to the removable panel 36 to the left of the terminal blocks 606 is a loop of 25 pair cable wires 608 having one end wired to the lower one of the terminal blocks 606. FIG. 14 illustrates the electrical wiring of this portion of the simulator 30.

For the Cable TV portion of this training program, a swing-out wall 610 is pivotally mounted to the sidewall 38 of the simulator 30. The swing-out wall 610 is intended to simulate various building surfaces and includes on one side thereof a panel 612 having aluminum siding 614, cedar clapboard 616 and cedar shingle shakes 618 mounted thereon one above the other. The panel 612 is mounted to the swing-out wall 610 using screws 620 to facilitate periodic replacement of the panel 612. The other side of the wall 610 is covered with a removable drywall panel 622.

The removable panel 48 in the top closure 42 of the simulator 30 has permanently installed thereon a messenger cable 624 which simulates a pole hook-up external to a residence.

In this section of the program the participant receives instructions in the installation of a coaxial TV cable from the pole line 624 to, and into, the house. The audiovisual presentation provides detailed, step-by-step instruction in using appropriate hand tools, preparing the ends of a coaxial messenger cable, drilling holes in sidings 614, 616, 618, installing cable clips, the screw hook, the wire loop and feed-through bushings, and finally in mounting the ground block and connecting the coaxial cable to it. After each step is presented, the filmstrip allows time for the participant to perform that procedure on the work-task simulator 30.

At several points in the filmstrip, the participant is told how to check his/her procedures and to correct them, if necessary. The participant is also advised to consult the instructor if he/she is having difficulty.

When a participant has performed any or all of the programs described above, he/she has received instructions as to how a career decision is made, i.e., what question should he/she ask him/herself in order to evaluate a particular career occupation. The participant also receives general information concerning each of the specific career occupations including the requirements, working conditions, and future job potential. Job-entry skills are also taught to the participant concerning the identification and handling of various occupationally-related tools and the job tasks likely to be encountered in each career occupation. In addition, the participant has received practical instructions on how to handle him/herself at an interview.

Numerous alterations of the structure herein-disclosed will suggest themselves to those skilled in the art. However, it is to be understood that the present disclosure relates to a preferred embodiment of the invention which is for purposes of illustration only and not to be construed as a limitation of the invention. All such modifications which do not depart from the spirit of the invention are intended to be included with the scope of the appended claims.

We claim:

1. A self-contained training system for providing a realistic simulated work environment and instructing a participant in the use of tools related to a specific occupation and in the performance of basic tasks related to that specific occupation, comprising:
   a folding cabinet including at least a rear wall and a base apron member adapted to support and partially enclose a participant when said cabinet is unfolded;
   components, materials and tools actually used in performing predetermined basic tasks in the specific occupation;
   means for mounting selected ones of the components and materials on the rear wall of said cabinet so as to simulate a work environment for the specific occupation, said simulated work environment being in need of tasks to be performed to change the physical characteristics of the components and materials; and
   means for presenting an assigned simulated job task to the participant for performance by the participant utilizing the tools on the components and materials so as to physically manipulate and change the character of the components and materials;

whereby the participant is given an opportunity to acquire actual experience in the specific occupation.

2. The self-contained training system according to claim 1 further comprising instructional material including an audiovisual device to reproduce information relating to the use of the components, materials and tools in performance of the simulated job task.

3. The self-contained training system according to claim 2 in which the instructional material further comprises printed material including self-assessment questionnaires on which the participant records the participant's own responses to questions concerning the specific occupation as well as self-assessment of the participant's own performance of the simulated job task.

4. The self-contained training system according to claim 1 wherein the specific occupation is electrical maintenance and further comprising means for selectively providing electrical power and case grounding to the cabinet.

5. The self-contained training system according to claim 1 wherein the specific occupation is building maintenance and further including representative wall covering materials typical of the type needing repair during the maintenance of a building, said wall covering materials being mounted on said cabinet.

6. The self-contained training system according to claim 1 wherein the specific occupation is insulation installation and further comprising structural means mounted on said cabinet for receiving various types of insulation.

7. The self-contained training system according to claim 1 wherein the specific occupation is housekeeping services and further including a wash basin and accompanying cabinet structure.

8. The self-contained training system according to claim 1 wherein the specific occupation is alarm and signal services and further including a window mounted on said cabinet.

9. The self-contained training system according to claim 1 wherein the specific occupation is alarm and signal services and further including a door mounted on said cabinet.

10. The self-contained training system according to claim 1 wherein the specific occupation is telephone and cable TV services and further including means mounted on said cabinet for simulating the exterior of a building.

* * * * *